(12) United States Patent
Jenkins (10) Patent No.: US 10,750,912 B2
(45) Date of Patent: Aug. 25, 2020

(54) DENTAL HYGIENE STORAGE DEVICE WITH SALT AND WATER DISPENSERS

(71) Applicant: Zachary Ryan Jenkins, Pittsburgh, PA (US)

(72) Inventor: Zachary Ryan Jenkins, Pittsburgh, PA (US)

(73) Assignee: Zachary Ryan Jenkins, Myrtle Beach, SC (US)

( * ) Notice: Subject to any disclaimer, the term of this patent is extended or adjusted under 35 U.S.C. 154(b) by 219 days.

(21) Appl. No.: 16/056,817

(22) Filed: Aug. 7, 2018

(65) Prior Publication Data

US 2020/0046175 A1 Feb. 13, 2020

(51) Int. Cl.
*A47K 5/18* (2006.01)
*A61Q 11/00* (2006.01)
(Continued)

(52) U.S. Cl.
CPC .............. *A47K 5/18* (2013.01); *A61C 19/066* (2013.01); *A61Q 11/00* (2013.01); *A46B 5/0095* (2013.01); *A46B 9/04* (2013.01); *A46B 2200/1066* (2013.01); *A47K 5/1202* (2013.01); *A61K 8/36* (2013.01); *A61K 2800/412* (2013.01)

(58) Field of Classification Search
CPC ...... A47K 5/18; A61C 19/063; A46B 5/0095; A61Q 11/00
See application file for complete search history.

(56) References Cited

U.S. PATENT DOCUMENTS

| | | | | | |
|---|---|---|---|---|---|
| 4,121,600 A | * | 10/1978 | Riddick | ............... | A47K 5/1214 132/310 |
| 5,215,193 A | * | 6/1993 | Dennis | ..................... | A47K 5/18 132/309 |
| 5,400,839 A | * | 3/1995 | Cravett | ..................... | A47K 5/18 132/314 |

* cited by examiner

Primary Examiner — Ryan A Reis

(57) ABSTRACT

The present invention relates to a dental hygiene storage device that dispenses a salt and water mouthwash on demand by use of a sensor or control buttons. Salt water rinses are one of the best routines we can practice reducing the effects of, and even preventing oral diseases. Sodium chloride is an antibacterial agent which inhibits the growth and multiplication of bacteria. In addition to bacteria, more recent research demonstrates that inflammation may be responsible for a multitude of periodontal diseases to which salt water rinses also remove inflammation from the gum tissues.

The invention consists of a compact base having an upstanding body, wherein the base is configured to rest on a horizontal support surface, such as a sink or countertop. The base may also include features used to mount the backside of the base to a vertical support surface, such as a wall.

In addition to storage areas for dental hygiene products, the base will include reservoirs, or reservoir assemblies therein. The reservoirs contain liquid and aggregates, primarily salt and water, but also suitable for other liquids such as mouthwash, and other particulates such as microbeads. The invention can have various ways of dispensing the salt and water from the reservoirs and by no means should the dispensing methods described and illustrated herein be considered limiting. The preferred embodiment defined herein dispenses the salt and water mouthwash into a cup which can rest on a stand integral to the base or held below the dispensers. The cup stand on the base may be adjustable to accommodate cups of various sizes, as well be removable.

7 Claims, 6 Drawing Sheets

(51) Int. Cl.
  *A61C 19/06* (2006.01)
  *A46B 9/04* (2006.01)
  *A47K 5/12* (2006.01)
  *A61K 8/36* (2006.01)
  *A46B 5/00* (2006.01)

DENTAL HYGIENE STORAGE DEVICE WITH SALT AND WATER DISPENSERS

CROSS-REFERENCE TO RELATED APPLICATION

Not Applicable.

BACKGROUND OF THE INVENTION

The present invention relates to dental hygiene storage and charging devices. More specifically, the present invention provides storage for, and a method of dispensing a mouthwash consisting of both a liquid and aggregate. In the preferred embodiment, the mouthwash consists of salt and water. The present invention provides a quick and effortless means of providing the mouthwash on demand in addition to providing storage for common items like tooth brushes, and flossing picks. Flossing picks are quickly becoming the standard in flossing paraphernalia, replacing traditional string floss and flossing methods with a much easier and effective approach.

It is necessary to exercise proper dental hygiene to prevent dental, and other diseases caused by bacteria that grows in the oral cavity. Either absorbed through the body or aspirated into the lungs, bacteria in the oral cavity can cause numerous systemic diseases. In addition to killing bacteria, salt water rinses also reduce inflammation of the gums. Recent research demonstrates that inflammation is also responsible for a multitude of periodontal diseases, which may lead to other systemic diseases.

Currently there is no convenient way to make a salt water mouthwash, especially in the bathroom where dental care takes place. Salt water rinses are an excellent preventative measure and treatment. The reason they are so good is that the salt is not only a natural disinfectant, but it also removes any swelling from the tissues. Sodium chloride is a powerful antibacterial agent. An antibacterial agent is one that inhibits the growth and multiplication of bacteria. Thus, the bacteria do not have a chance to grow and flourish as much. The salt crystals also act like a detergent, or micro scrubber, that cleans between the smallest and inaccessible spaces by swishing the salt water mouthwash between the teeth vigorously.

Flossing daily is also an essential step in cleaning between the teeth and below the gum line to remove bacterial or dental plaque. Dental authorities consider plaque the leading cause of periodontal disease and tooth loss in adults.

However, current flossing methods require one to tightly string a line between both hands to effectively clean between one tooth at a time. This requires some skill and patience. It can also be damaging if done incorrectly. Flossing picks are quickly becoming standard for flossing as they provide a much easier user experience that is more effective than traditional flossing. Even with the advent of flossing picks, flossing is still seen as tedious, and time consuming. A need exists to store them, on display as a reminder to floss daily. A salt water mouthwash rinse is also a great way to floss when time is short. Currently no dental hygiene storage device provides a means for storing and dispensing the necessary items to make a salt water mouthwash on demand, as well provide storage and electrical charging for modern dental hygiene products. Thus, an improved dental hygiene storage device is desired.

Devices have been disclosed in the prior art that relate to dental hygiene storage and organizing devices. These include devices that have been patented and published in patent application publications. These devices generally relate to dental hygiene holding devices having various configurations for storing toothbrushes and other items, such as U.S. Pat. No. 9,629,506 B1, U.S. Pat. No. 5,629,527 A, and US Patent Application No. US 2004/0050733A1.

These prior art devices have several known drawbacks. The devices in the prior art fail to provide a means for storing aggregates, most commonly table salt, water, and/or mouthwash with a means of dispensing the contents on demand. Further, the prior art devices fail to provide a power supply or power input. The preferred embodiment of the present invention contains electric motors and pumps used to dispense liquids and aggregates. In this preferred embodiment the power supply and liquid reservoirs can also be utilized to charge, and power other electronic dental hygiene products stored within the device such as electronic toothbrushes or water flossing picks.

Considering the devices disclosed in the prior art, it is submitted that the present invention substantially diverges in design elements from the prior art and consequently it is clear that there is a need in the art for an improvement to existing dental hygiene storage devices. In this regard the instant invention substantially fulfills these needs.

SUMMARY OF THE INVENTION

In view of the foregoing disadvantages inherent in the known types of dental hygiene storage devices now present in the prior art, the present invention provides a new dental hygiene storage device wherein the same can be utilized for providing convenience for the user when storing, organizing and dispensing dental hygiene products.

The present invention provides a dental hygiene storage device for use in storing and organizing toothbrushes, flossing picks, aggregates such as table salt, and liquids such as mouthwash, or water, among other related items. The storage device comprises a base having an upstanding body extending therefrom. The upstanding body comprises a toothbrush holder thereon for holding one or more toothbrushes in a vertical orientation. The base comprises one or more recesses for storing flossing picks therein. The base also contains reservoirs, or reservoir assemblies which aggregates, and liquids may be stored. Further, the invention provides a means of dispensing stored contents on demand.

Other objects, features, and advantages of the present invention will become apparent from the following detailed description taken in conjunction with the accompanying drawings.

BRIEF DESCRIPTION OF THE SEVERAL VIEWS OF THE DRAWING

Although the characteristic features of this invention will be particularly pointed out in the claims, the invention itself and way it might be made and used may be better understood after a review of the following description, taken in connection with the accompanying drawings wherein like numeral annotations are provided throughout.

DETAILED DESCRIPTION OF THE INVENTION

Reference is made herein to the attached drawings. Reference numerals are used throughout the drawings to depict like or similar elements of the dental hygiene storage device. For the purposes of presenting a brief and clear description of the present invention, the preferred embodiment will be discussed as used for dispensing a salt water mouthwash and storing of various types of dental hygiene products, such as toothbrushes, flossing picks, mouthwash, rinsing cup and the like. The figures are intended for representative purposes only and should not be considered limiting in any respect.

Figure 1:
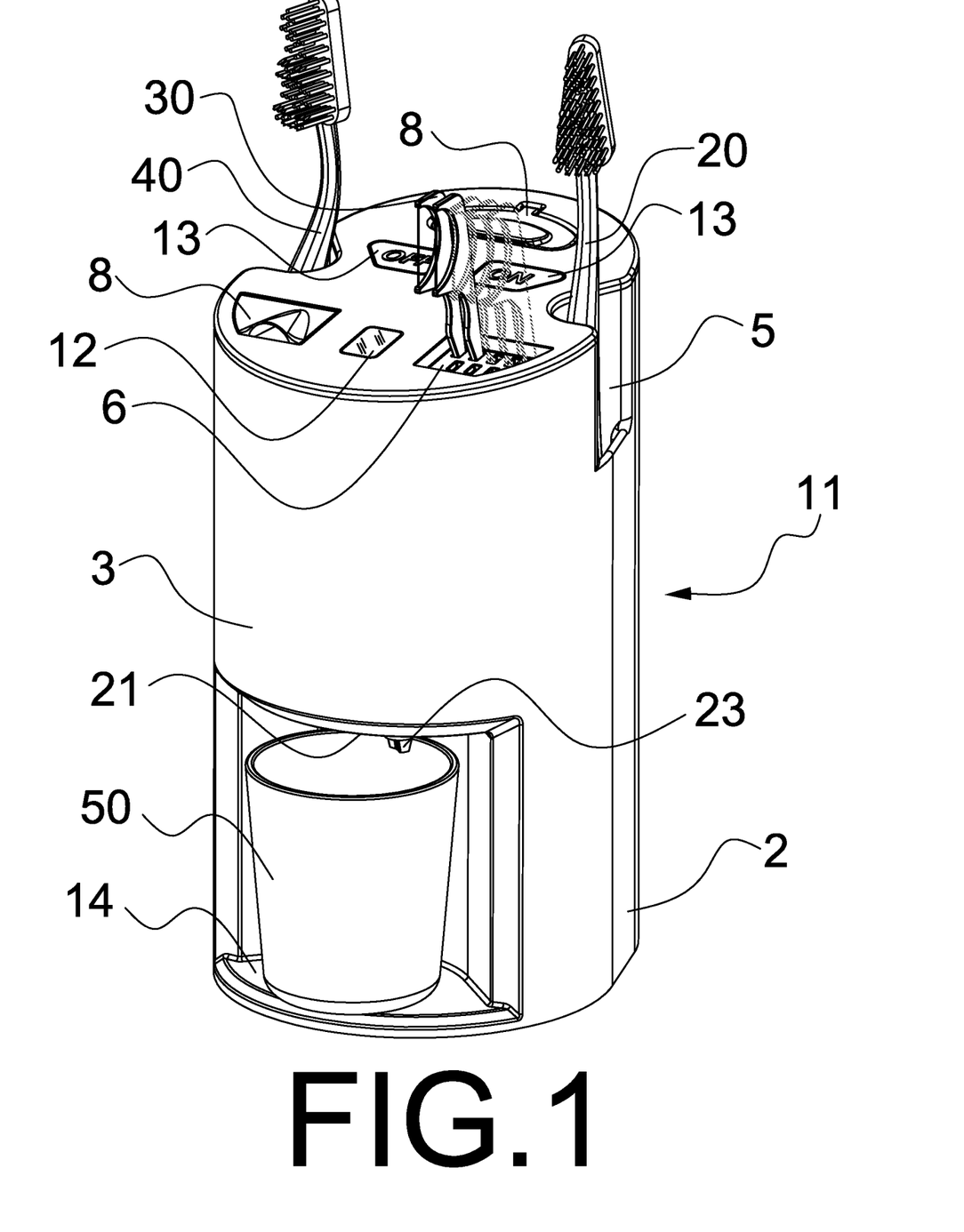
FIG. 1 shows a front perspective view of the dental hygiene storage device.

Referring now to FIG. 1, there is shown a front perspective view of the dental hygiene storage device 11. The dental hygiene storage device 11 comprises a base 2 having an upstanding body 3 extending therefrom. The upstanding body 3 extends vertically upward from the base 2. The dental hygiene storage device 11 can be positioned on a horizontal support surface such as a counter or sink, wherein the base 2 stabilizes the storage device 11 in an upright orientation. Alternatively, the user can affix the rear mounting surface 4 to a vertical support surface, such as a wall, for securing the dental hygiene storage device 11 thereon. The rear mounting surface 4 of the upstanding body 3 can be affixed to a wall via any conventional fastening methods such as by use of adhesives, fasteners such as screws, bolts, or nails, or via brackets.

Figure 2:
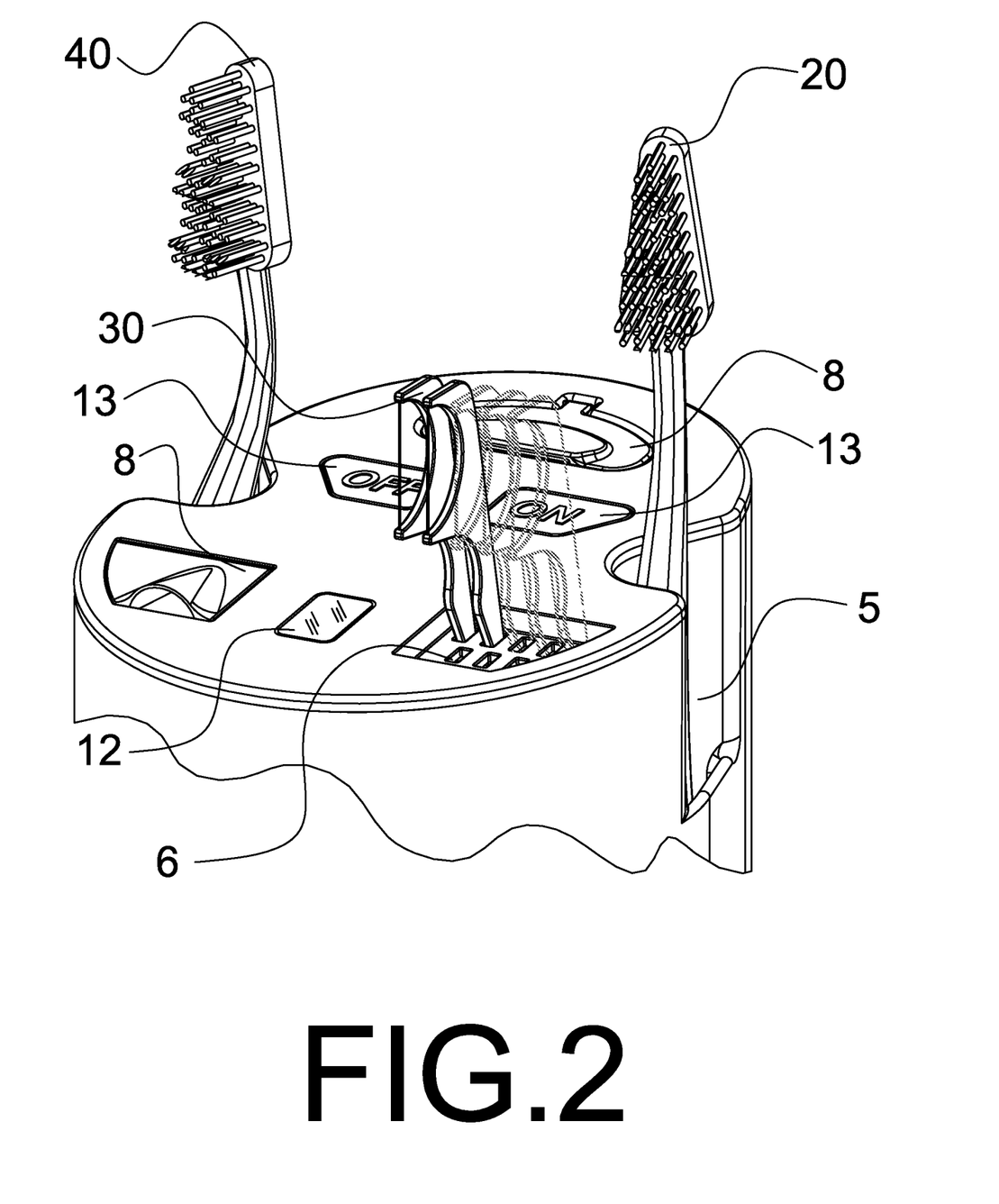
FIG. 2 shows a close-up view of the top surface shown in FIG. 1.

The upstanding body 3 comprises a toothbrush holder 5 and flossing pick holder 6 on a top surface thereof. The toothbrush holder 5 comprises one or more recesses adapted to removably receive a portion of a toothbrush 20 therein. The flossing pick holder 6 comprises one or more openings to removably receive a portion of a flossing pick 30 therein. The toothbrush holder 5 may double as a charging port 7 for electric tooth brushes 40. The toothbrush holder 5 is shaped as such to easily guide the electric toothbrush 40 onto the charging port 7.

The upstanding body 3 comprises closable openings 8 for filling the aggregate reservoir 9 and liquid reservoir assembly 10. The closeable openings 8 provide easy access to fill the reservoirs on a top surface. Furthermore, the top surface contains an infrared sensor assembly 12, and control buttons 13. The infrared sensor assembly 12 can be used to easily activate the dental hygiene device 11 by waving your hand, dispensing the reservoir contents. The control buttons 13 provide a means to turn the device on or off, as well control the volume that is dispensed when activating the dental hygiene device 11 via the infrared sensor assembly 12. Furthermore, the upstanding body 3 comprises a recessed platform 14 to which a cup 50 can be stored below the liquid dispenser 23 and aggregate dispensing shaft 21.

Figure 3:
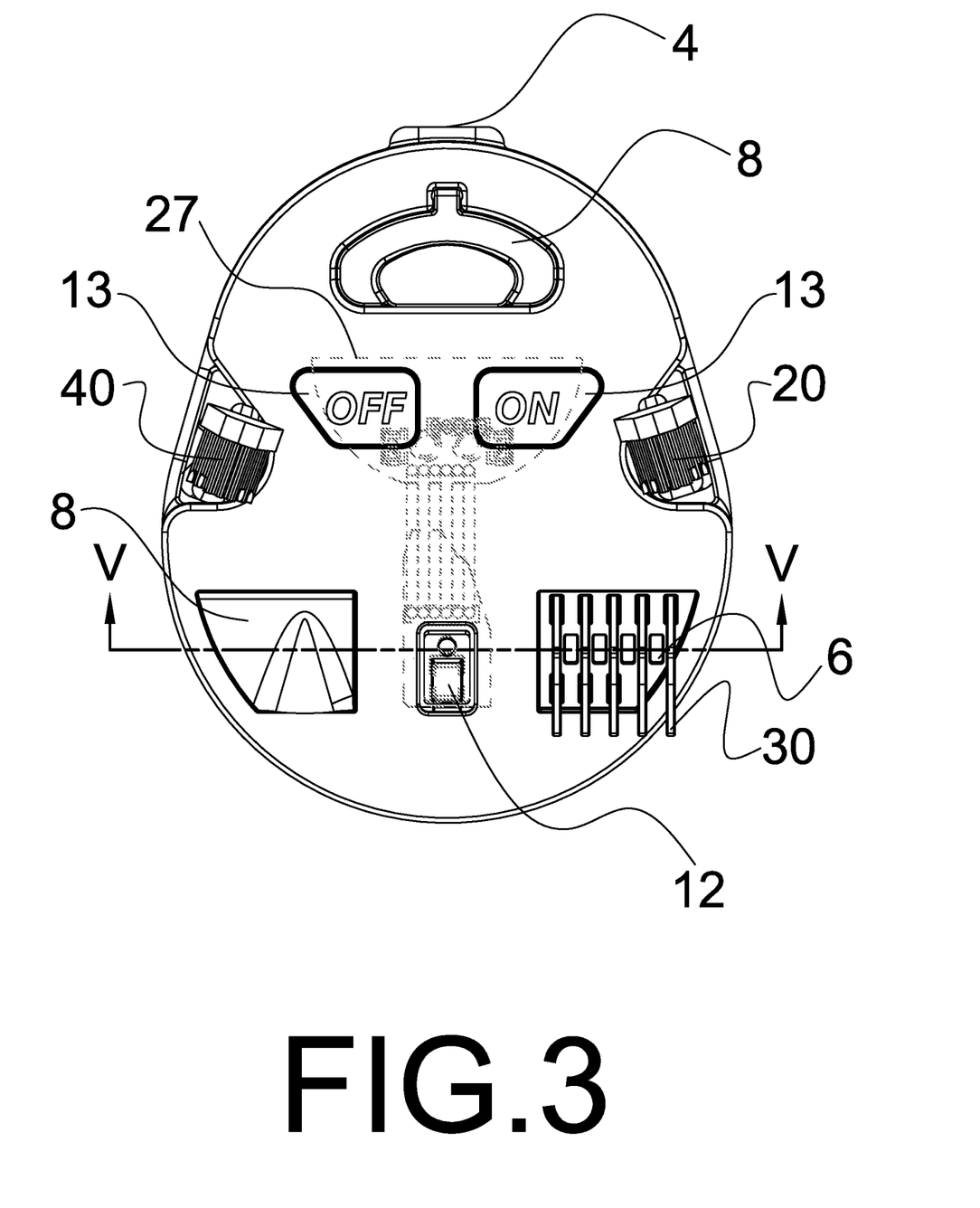
FIG. 3 shows a top orthographic view of the dental hygiene storage device.

Referring now to FIG. 3, showing a top orthographic projection of the top surface. The infrared sensor assembly 12 located at the front of the top surface can be used to dispense reservoir contents by simply waving hand past infrared sensor assembly 12. The infrared sensor assembly 12 is wired to a control board assembly 27. The closable openings 8 located to the left of the infrared sensor 12 and at the back of the top surface can be opened by the user to refill liquids and aggregates then closed to keep the reservoirs free from unwanted contaminates. The flossing pick holder 6 is shown to the right of the infrared sensor assembly 12. The openings of the flossing pick holder 6 are sized to accept the pick end of the flossing pick 30 orienting it vertically and stopping the pick at the thicker portion of it's extension or at the forked portion of the flossing pick 30. The control buttons 13 are shown in the middle of the top surface located above the control board assembly 27.

Figure 4:
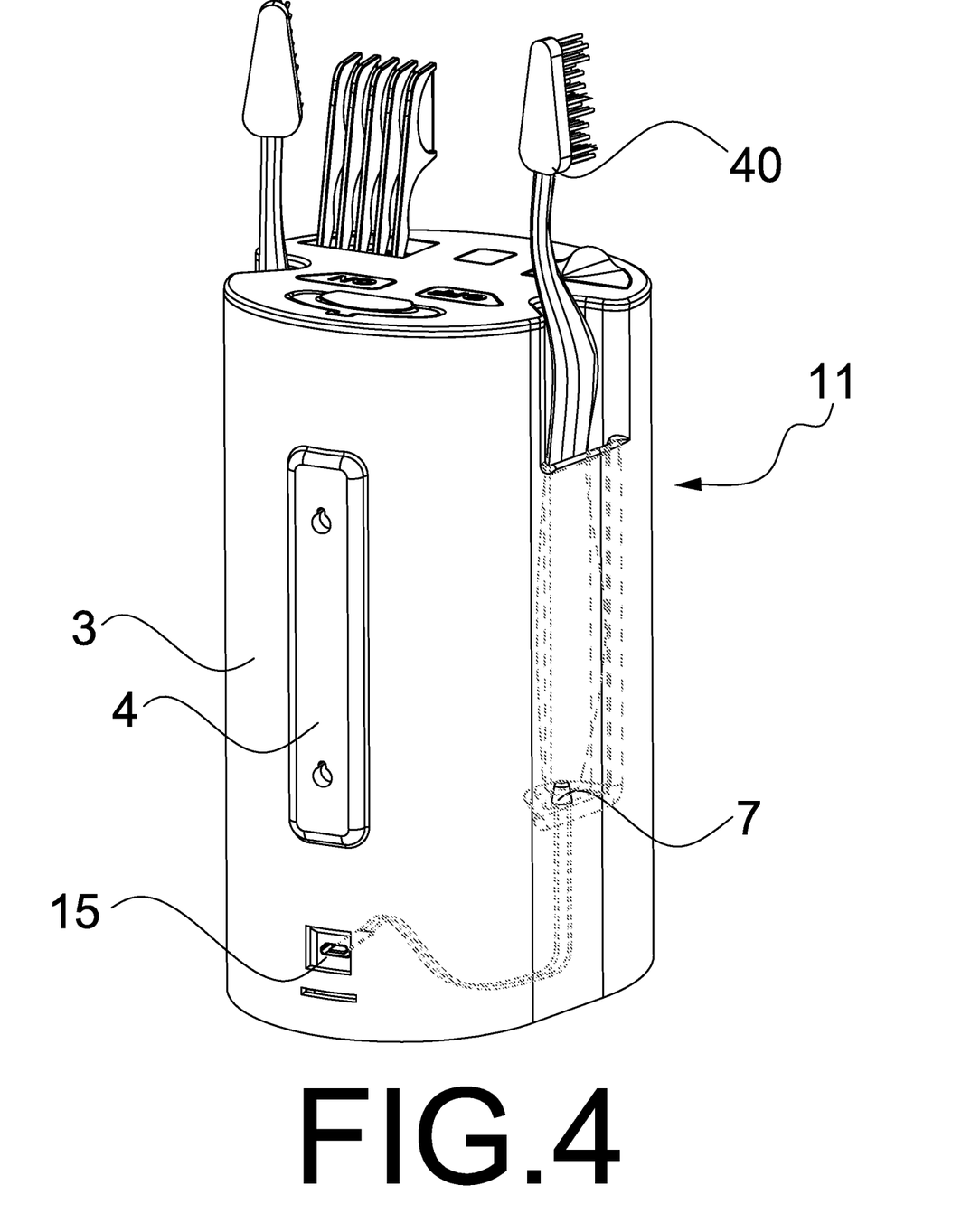
FIG. 4 shows a rear perspective view of the dental hygiene storage device.

Referring now to FIG. 4, showing a rear perspective view, the power supply input 15 is shown at the bottom of the upstanding body 3. The power supply input 15 can be used for directly powering the device and charging the rechargeable battery 16, as well charging other electrically powered dental hygiene devices such as an electric toothbrush 40. The rear mounting surface 4 is shown above the power port 15. On the right-hand side, the electric toothbrush 40 and charging port 7 are shown.

Figure 5:
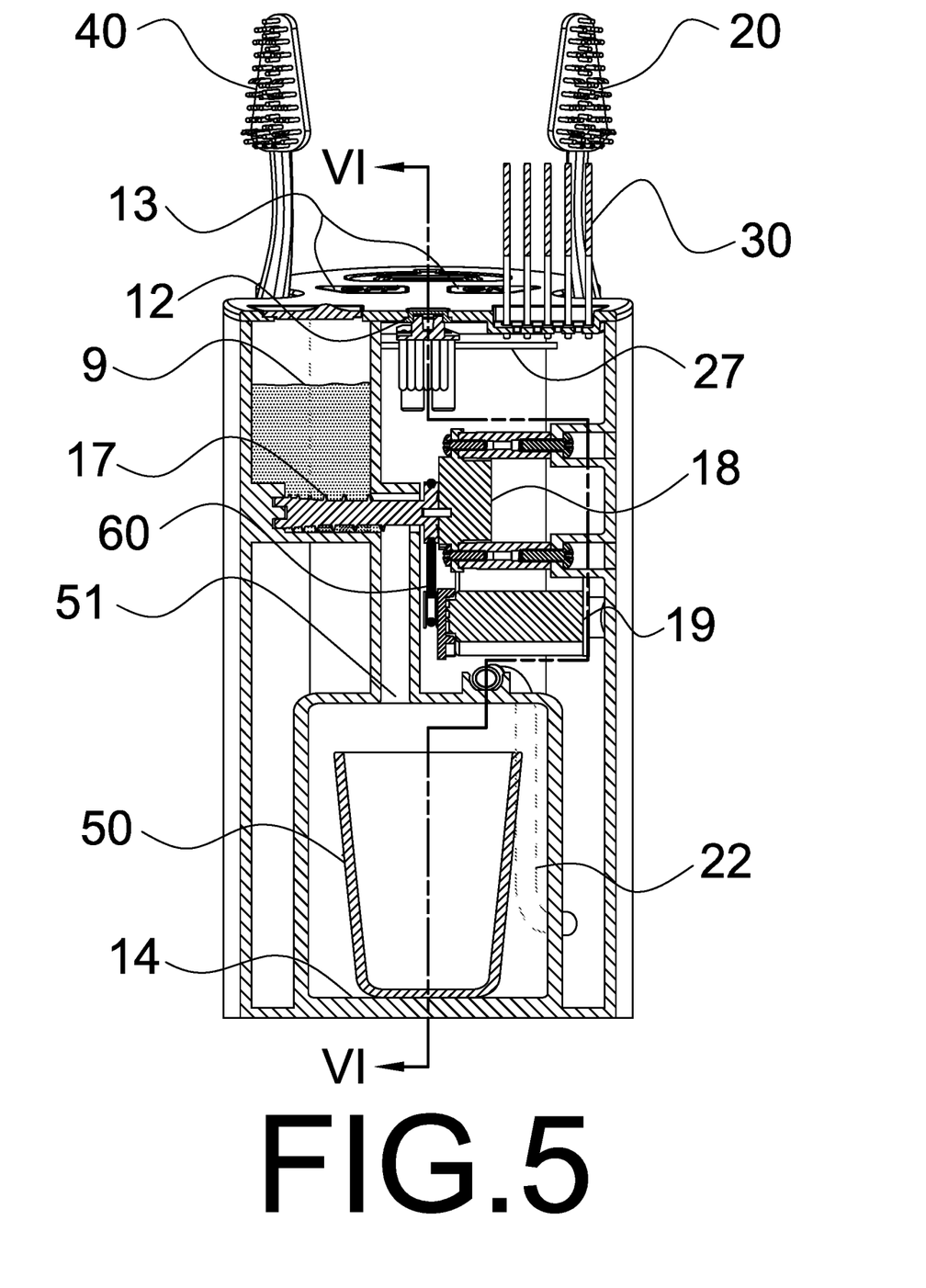
FIG. 5 shows a front orthographic projection from FIG. 3 sectioned by line V-V.

Referring now to FIG. 5, the cross section shows the aggregate reservoir 9, dispensing screw 17, dispensing screw gearbox 18, dispensing screw electric motor 19, and aggregate dispensing shaft 21. The dispensing screw electric motor 19 is wired to the control board assembly 27. When the infrared sensor 12 is activated, or the control buttons 13 are pressed, the control board assembly 27 provides power to the dispensing screw electric motor 19. The dispensing screw electric motor 19 turns the dispensing screw 17 via a belt 60 attached to the dispensing screw gearbox 18 and dispensing screw electric motor 19. The dispensing screw 17 pulls aggregates from the aggregate reservoir 9 dropping aggregates down the aggregate dispensing shaft 51 into a cup 50, which rests on the platform 14.

Figure 6:
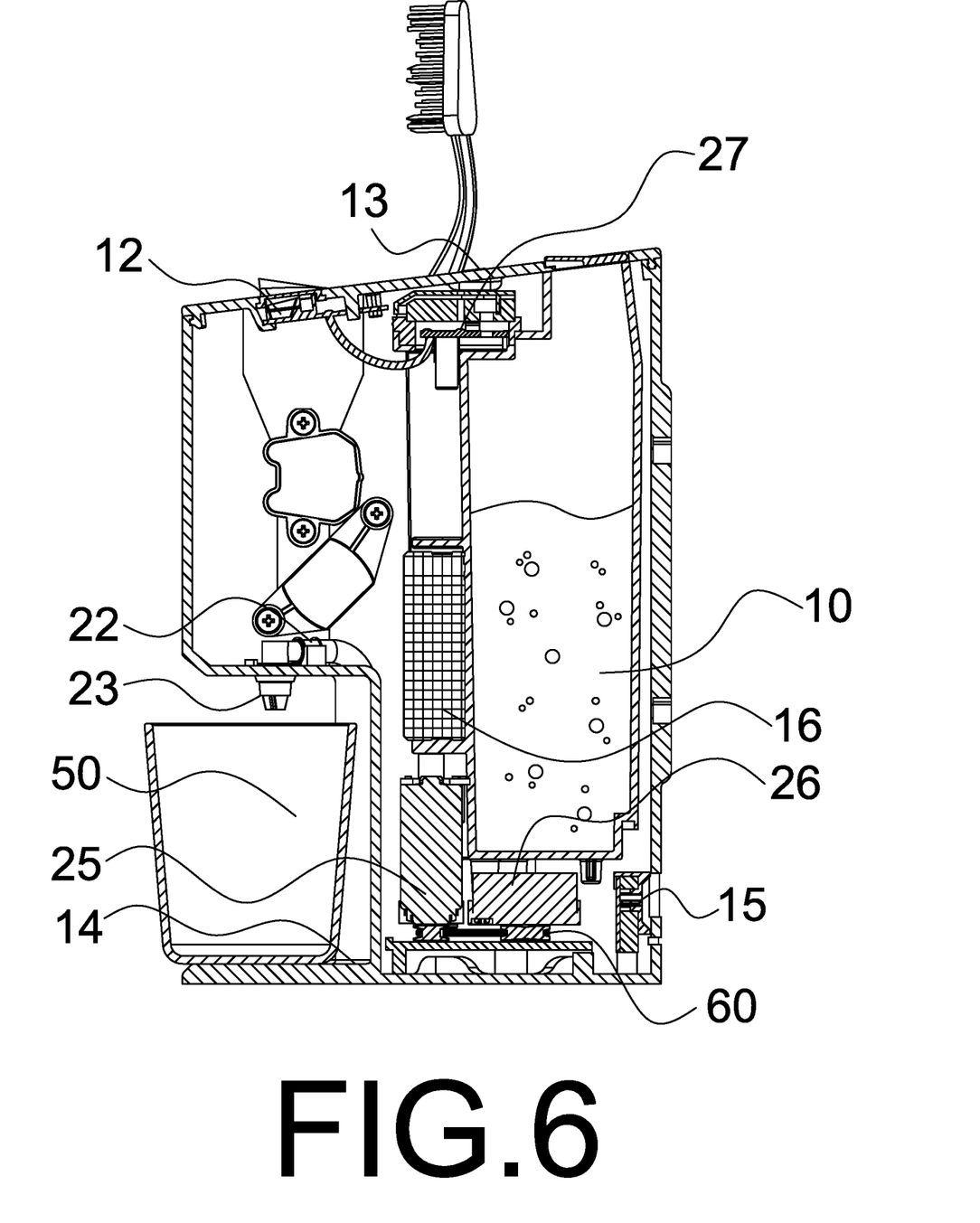
FIG. 6 shows a right orthographic projection from FIG. 5 sectioned by line VI-VI.

Referring now to FIG. 6, the cross section shows the liquid reservoir assembly 10, infrared sensor assembly 12, rechargeable battery 16, pump electric motor 25, pump 26, control board assembly 27, and power supply input 15. The pump electric motor 25 is wired to the control board assembly 27. When the infrared sensor 12 is activated, or the control buttons 13 are pressed, the control board assembly 27 provides power to the pump electric motor 25. The pump electric motor 25 turns the pump 26 via a belt 60 attached to the pump 26 and pump electric motor 25. The pump 26 draws liquid from the liquid reservoir assembly 10 and pumps it through the liquid dispensing hose 22 and dispenses the liquid via the liquid dispenser 23 into a cup 50, which rests on the platform 14.

It is therefore submitted that the instant invention has been shown and described in what is the most practical and preferred embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed clear and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

The invention claimed is:

1. A dental hygiene storage device, comprising:
a base having an upstanding body extending therefrom;

the base having an open area or platform where a cup can be placed beneath the upstanding body;

the upstanding body having aggregate and liquid reservoirs with means to dispense contents from the reservoirs via dispensers positioned above the base;

the upstanding body having a sloped top surface orienting control buttons, closable lids, a sensor, and a flossing pick holder towards a user;

the closable lids are pivotally affixed to the top surface, located above the reservoirs adapted for aggregate and liquid storage therein;

toothbrush holders are recessed into opposite sides of the upstanding body, open at the top surface extending downward towards the base, orienting a toothbrush or toothbrushes in a vertical fashion.

2. The dental hygiene storage device of claim 1, wherein the dispenser are operated mechanically.

3. The dental hygiene storage device of claim 1, wherein the dispenser are electro mechanically operated via the sensor or the control buttons.

4. The dental hygiene storage device of claim 3, where the sensor is activated by infrared, photo or radar-based sensing.

5. The dental hygiene storage device of claim 3, where the sensor is activated by audible sensing.

6. The dental hygiene storage device of claim 3, where the toothbrush holder has a charging port affixed to the bottom of the recessed cavity for charging an electric toothbrush.

7. The dental hygiene storage device of claim 1, wherein the flossing pick holder comprises one or more openings thereon adapted to removably secure a portion of a flossing pick therein via frictional fit.

* * * * *